United States Patent
Miller et al.

(10) Patent No.: US 7,148,477 B2
(45) Date of Patent: Dec. 12, 2006

(54) SYSTEM FOR TRAJECTORY-BASED ION SPECIES IDENTIFICATION

(75) Inventors: Raanan A. Miller, Newton, MA (US); Erkinjon G. Nazarov, Lexington, MA (US); Lawrence A. Kaufman, Waltham, MA (US)

(73) Assignee: Sionex Corporation, Bedford, MA (US)

( * ) Notice: Subject to any disclaimer, the term of this patent is extended or adjusted under 35 U.S.C. 154(b) by 121 days.

(21) Appl. No.: 10/840,829

(22) Filed: May 7, 2004

(65) Prior Publication Data

US 2005/0029449 A1 Feb. 10, 2005

Related U.S. Application Data

(63) Continuation-in-part of application No. 10/278,738, filed on Oct. 22, 2002, now abandoned, and a continuation-in-part of application No. 10/187,464, filed on Jun. 28, 2002, now Pat. No. 7,045,776, which is a continuation-in-part of application No. 09/896,536, filed on Jun. 30, 2001, now abandoned, and a continuation-in-part of application No. 10/321,822, filed on Dec. 16, 2002, now Pat. No. 6,806,463, which is a continuation-in-part of application No. 09/358,312, filed on Jul. 21, 1999, now Pat. No. 6,495,823, and a continuation-in-part of application No. 10/082,803, filed on Feb. 21, 2002, now Pat. No. 6,815,669, which is a continuation-in-part of application No. 09/439,543, filed on Nov. 12, 1999, now Pat. No. 6,512,224, which is a continuation-in-part of application No. 09/358,312, filed on Jul. 21, 1999, now Pat. No. 6,495,823.

(60) Provisional application No. 60/336,522, filed on Oct. 23, 2001, provisional application No. 60/336,506, filed on Oct. 23, 2001, provisional application No. 60/351,043, filed on Jan. 23, 2002, provisional application No. 60/334,685, filed on Nov. 15, 2001, provisional application No. 60/340,894, filed on Oct. 30, 2001.

(51) Int. Cl.
*B01D 59/44* (2006.01)
*H01J 49/00* (2006.01)
*H01J 49/28* (2006.01)

(52) U.S. Cl. .................. 250/294; 250/293; 250/282

(58) Field of Classification Search ........ 250/290–294, 250/282

See application file for complete search history.

(56) References Cited

U.S. PATENT DOCUMENTS 2,615,135 A 10/1952 Glenn
3,511,986 A 5/1970 Llewellyn (Continued)

FOREIGN PATENT DOCUMENTS

SU 966583 10/1982

(Continued)

OTHER PUBLICATIONS

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

(Continued)

*Primary Examiner*—Jack Berman
*Assistant Examiner*—Jennifer Yantorno
(74) *Attorney, Agent, or Firm*—Fish & Neave IP Group, Ropes & Gray LLP

(57) ABSTRACT

Method and apparatus for field ion mobility spectrometry for identification of chemical compounds in a sample by trajectory of sample ions in a transverse electric field.

22 Claims, 5 Drawing Sheets

U.S. PATENT DOCUMENTS

| | | | |
|---|---|---|---|
| 3,621,240 A | | 11/1971 | Cohen et al. |
| 3,931,589 A | | 1/1976 | Aisenberg et al. |
| 4,025,818 A | | 5/1977 | Giguere et al. |
| 4,201,921 A | | 5/1980 | McCorkle |
| 5,420,424 A | * | 5/1995 | Carnahan et al. ............ 250/287 |
| 5,455,417 A | | 10/1995 | Sacristan |
| 5,536,939 A | | 7/1996 | Freidhoff et al. |
| 5,654,544 A | | 8/1997 | Dresch |
| 5,723,861 A | | 3/1998 | Carnahan et al. |
| 5,763,876 A | | 6/1998 | Perinarides et al. |
| 5,789,745 A | | 8/1998 | Martin et al. |
| 5,801,379 A | | 9/1998 | Kouznetsov |
| 5,834,771 A | | 11/1998 | Yoon et al. |
| 5,838,003 A | | 11/1998 | Bertsch et al. |
| 5,965,882 A | | 10/1999 | Megerle et al. |
| 6,066,848 A | | 5/2000 | Kassel et al. |
| 6,107,624 A | * | 8/2000 | Doring et al. ............... 250/286 |
| 6,124,592 A | * | 9/2000 | Spangler ..................... 250/287 |
| 6,323,482 B1 | | 11/2001 | Clemmer et al. |
| 6,495,823 B1 | | 12/2002 | Miller et al. |
| 6,504,149 B1 | | 1/2003 | Guevremont et al. |
| 6,509,562 B1 | | 1/2003 | Yang et al. |
| 6,512,224 B1 | * | 1/2003 | Miller et al. ................. 250/286 |
| 6,621,077 B1 | | 9/2003 | Guevremont et al. |
| 6,639,212 B1 | | 10/2003 | Guevremont |
| 6,653,627 B1 | | 11/2003 | Guevremont |
| 6,690,004 B1 | | 2/2004 | Miller et al. |
| 6,703,609 B1 | | 3/2004 | Guevremont |
| 6,713,758 B1 | | 3/2004 | Guevremont |
| 6,753,522 B1 | | 6/2004 | Guevremont |
| 6,770,875 B1 | | 8/2004 | Guevremont |
| 6,774,360 B1 | | 8/2004 | Guevremont |
| 6,787,765 B1 | | 9/2004 | Guevremont |
| 6,799,355 B1 | | 10/2004 | Guevremont |
| 6,806,466 B1 | | 10/2004 | Guevremont |
| 2001/0030285 A1 | | 10/2001 | Miller et al. |
| 2002/0070338 A1 | | 6/2002 | Loboda |
| 2002/0134932 A1 | | 9/2002 | Guevremont et al. |
| 2003/0020012 A1 | | 1/2003 | Guevremont et al. |
| 2003/0038235 A1 | | 2/2003 | Guevremont et al. |
| 2003/0052263 A1 | | 3/2003 | Kaufman et al. |
| 2003/0089847 A1 | | 5/2003 | Guevremont et al. |
| 2003/0132380 A1 | | 7/2003 | Miller et al. |
| 2004/0094704 A1 | | 5/2004 | Miller et al. |

FOREIGN PATENT DOCUMENTS

| | | |
|---|---|---|
| SU | 1337934 A2 | 9/1987 |
| SU | 1627984 A2 | 7/1988 |
| SU | 1412447 A1 | 6/1998 |
| SU | 1485808 | 10/1998 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/071053 A2 | 9/2002 |
| WO | WO 02/083276 A1 | 10/2002 |
| WO | WO 03/005016 A1 | 1/2003 |
| WO | WO 03/015120 A1 | 2/2003 |

OTHER PUBLICATIONS

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Barnett, D.A. et al., "Isotope Separation Using High-Field Asymmetric Waveform Ion Mobility Spectrometry," Nuclear Instruments & Methods in Physics Research (2000), pp. 179-185, 450(1).

Buryakov, I.A. et al., "Separation Ions According to Mobility in a Strong ac electric Field," Sov. Tech. Phs. Lett. (1991), pp. 446-447, 17(6).

Buryakov, I.A. et al., "Device and Method For Gas Electrophoresis, Chemical Analysis of Environment," edit. Prof. V.V. Malakhov, Novosibirsk; Nauka (1991), pp. 113-127.

Buryakov, I.A. et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes (1993), pp. 143-148, 128.

Carnahan, B. et al., "Field Ion Spectrometry—A New Analytical Technology for Trace Gas Analysis," ISA, (1996), PP. 87-96, 51(1).

Carnahan, B. et al., "Field Ion Spectrometry—A New Technology for Cocaine and Heroin Detection," SPIE, (1997), pp. 106-119, 2937.

Eiceman, G.A., et al., "Miniature radio-frequency mobility analyzer as a gas chromatographic detector for oxygen-containing volatile organic compounds, pheromones, and other insect attractants," J. Chromatography, (2001), pp. 205-217, 917.

Guevremont, R. and Purves, R., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R. et al., "Atmospheric Pressure In Focusing in a High-Field Asymmetric Waveform Ion Mobility Spectrometer," Review of Scientific Instruments, (1999), pp. 1370-1383, 70(2).

Handy, Russell et al., "Determination of nanomlar levels of perchlorate in water by ESI-FAIMS-MS," JAAS (2000), pp. 907-911, 15.

Hathout, Y., et al., "Identification of Bacillus Spores by Matrix-Assisted Laser Desorption Ionization Mass Spectrometry," Appl. Environ. Microbiol. 65(10):4313-4319 (1999).

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio-frequency ion mobility spectrometer for chemical vapor detection," Sensors and Actuators, (2001), pp. 301-312, A91.

Miller, R.A. et al., "A Novel Micromachined High-Field Asymmetric Waveform-Ion Mobility Spectrometer," Sensors and Actuators B, (2000) pp. 300-306, B67 (3).

Pilzecker, P. et al., "On-Site Investigations of Gas Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., "High Sensitivity GC-FIS for Simultaneous Detection of Chemical Warfare Agents," Mine Safety Appliances Co., Pittsburgh, PA, USA, (2000), AT-Process, pp. 124-136, 5(3,4), CODEN: APJCFR ISSN: 1077-419X.

* cited by examiner

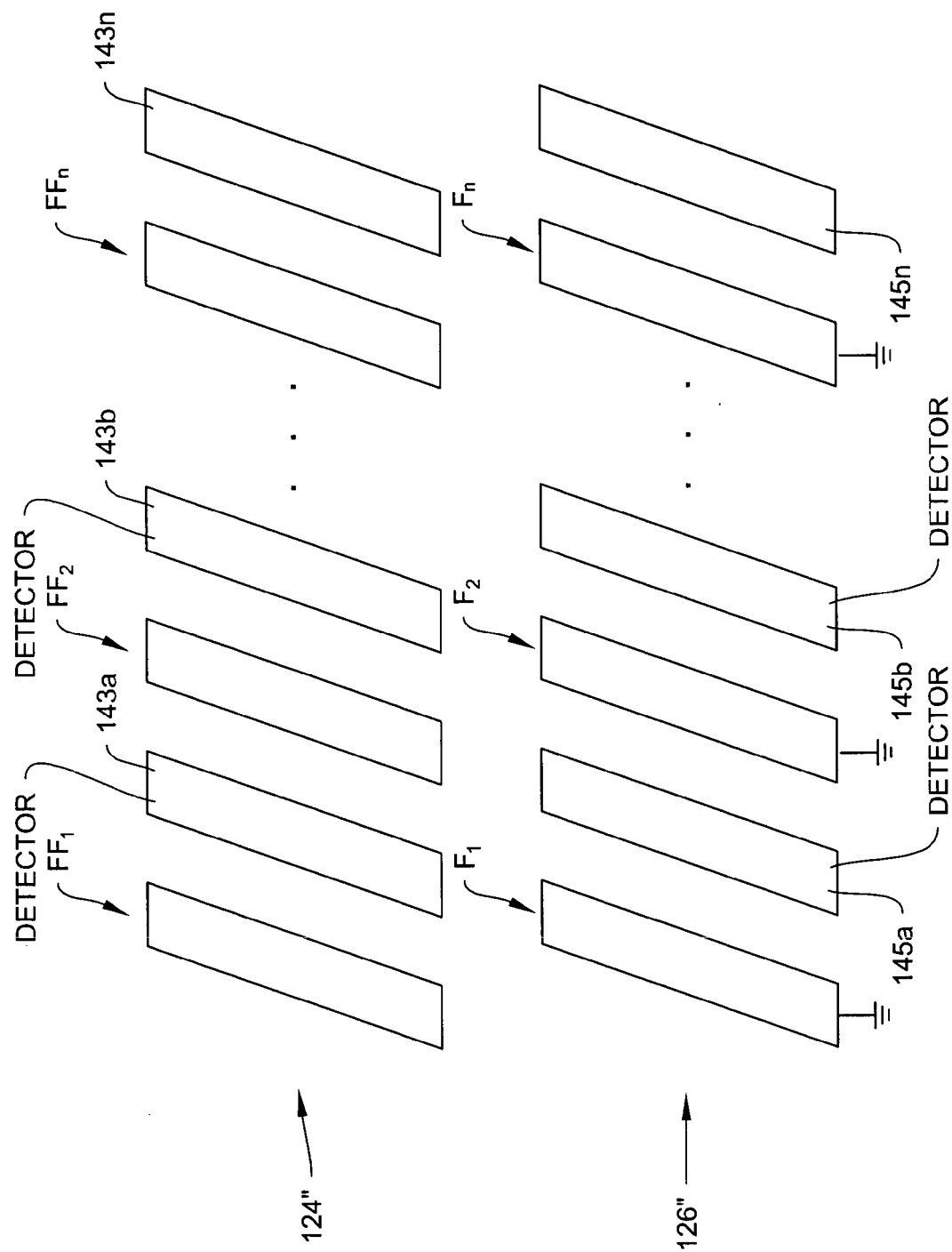

SYSTEM FOR TRAJECTORY-BASED ION SPECIES IDENTIFICATION

CROSS REFERENCE OF RELATED APPLICATIONS

This application is a continuation-in-part of U.S. application Ser. No. 10/278,738, filed Oct. 22, 2002, now abandoned which is a continuation-in-part of U.S. application Ser. No. 10/187,464, filed Jun. 28, 2002, now U.S. Pat. No. 7,045,776 which is a continuation-in-part of U.S. application Ser. No. 09/896,536, filed Jun. 30, 2001, now abandoned and which claims the benefit of U.S. Provisional Application No. 60/340,894, filed Oct. 30, 2001, U.S. Provisional Application No. 60/334,685, filed Nov. 15, 2001, U.S. Provisional Application No. 60/351,043, filed Jan. 23, 2002, and also claims the benefit of U.S. Provisional Application No. 60/336,506, filed Oct. 23, 2001, and U.S. Provisional Application No. 60/336,522, filed Oct. 23, 2001.

This application is a continuation-in-part of U.S. application Ser. No. 10/321,822, filed Dec. 16, 2002, now U.S. Pat. No. 6,806,463 which is a continuation of U.S. application Ser. No. 09/358,312, filed Jul. 21, 1999 (now issued U.S. Pat. No. 6,495,823, issued Dec. 17, 2002).

This application is also a continuation-in-part of U.S. application Ser. No. 10/082,803, filed Feb. 21, 2002, now U.S. Pat. No. 6,815,669 which is a continuation-in-part of U.S. application Ser. No. 09/439,543, filed Nov. 12, 1999 (now issued U.S. Pat. No. 6,512,224, issued Jan. 28, 2003), which is a continuation-in-part of the above U.S. application Ser. No. 09/358,312.

The entire contents of all of the above applications are incorporated herein by reference in their entirety.

BACKGROUND OF THE INVENTION

The present invention relates generally to identification of unknown members of a sample by mobility characteristics, and more particularly to devices that analyze compounds via field-based ion mobility spectrometry.

There are a number of different circumstances in which it is desirable to perform a chemical analysis to identify compounds in a sample. Such samples may be taken directly from the environment or they may be provided by specialized front-end devices that separate or prepare compounds before analysis.

Furthermore, recent events have seen members of the general public exposed to dangerous chemical compounds in situations where previously no thought was given to such exposure. There exists, therefore, a demand for accurate, easy to use, and reliable devices capable of detecting the chemical makeup of a sample rapidly and even at trace levels, whether in the laboratory or in the field.

Mass spectrometers are generally recognized as highly accurate detectors for compound identification, given that they can generate a fingerprint pattern for even fragment ions. However, mass spectrometers are quite expensive, easily exceeding a cost of $100,000 or more and are physically large enough to become difficult to deploy everywhere the public might be exposed to dangerous chemicals. Mass spectrometers also suffer from other shortcomings such as the need to operate at relatively low pressures, resulting in complex support systems. They also need a highly trained operator to tend to and interpret the results. Accordingly, mass spectrometers are generally difficult to use outside of laboratories.

A class of chemical analysis instruments more suitable for field operation operate based upon aspects of ion mobility in an analytical field. One such type is known as Field Asymmetric Ion Mobility Spectrometers (FAIMS) (also known as Radio Frequency Ion Mobility Spectrometers (RFIMS) and Differential Mobility Spectrometers (DMS), among other names. This type of spectrometer subjects an ionized sample to a compensated varying high-low asymmetric electric field and filters ions based on aspects of their field mobility.

Typically a gas sample flows through a varying high asymmetric RF field which allows only selected ion species to pass through, according to an applied low DC compensation voltage, and specifically only those ions that exhibit selected mobility responses in the field. An ion detector then collects detection data for the detected ions. This may include intensity data shown as detection "peaks." These peaks are interpreted according to the compensation voltage at which a species of ion is able to pass through an asymmetric field of given field parameters.

A typical FAIMS device includes a pair of electrodes in a drift tube. An asymmetric field is applied to the electrodes transverse to the ion flow path. The asymmetric RF field alternates between a high or "peak" field strength and a low field strength. The field varies with a particular frequency and duty cycle. Field strength varies as the applied voltage and size of the analytical gap between the electrodes.

In a FAIMS device, ions will pass through the analytical gap between the electrodes only when their net transverse displacement per period of the asymmetric field is zero; in contrast, ions that undergo a net displacement will eventually undergo collisional neutralization on one of the electrodes. In a given RF asymmetric field, a displaced ion can be restored to the center of the gap (i.e. compensated, with no net displacement for that ion) when a low strength DC electric field (the compensation voltage, Vcomp) is superimposed on the RF. Ions with differing displacement (owing to characteristic dependence of mobility in the field) can be passed through the gap at compensation voltages characteristic of a particular ion, which is accomplished by applying various strengths of Vcomp. With Vcomp held at one value, the system can function as a continuous ion filter, or a scan of Vcomp will allow complete measure of the spectrum of ion species in the sample. The recorded image of the spectral scan of the sample is sometimes referred to as a "mobility scan" or as an "ionogram".

The detected compounds can be identified by comparing detection data against a library, for example, of stored known identification data. By noting the RF level and compensation voltage and the corresponding detected signal, an ion species can be identified, as well as concentration level (as seen in the detection peak characteristics). Ideally a specific RF level and compensation voltage will permit only a particular species of ion (according to signature mobility in the field) to pass through the filter to the detector. However, if mobilities overlap under the selected field conditions, then the detected species may contain ions for several compounds happening to have the same mobility under those conditions. This can result in detection errors, sometimes referred to as "false positives".

It is an object of the invention to provide a simple and compact apparatus to achieve such detections with improved accuracy.

It is another object of the invention to provide an improved ion species detection device with higher sensitivity and reduced false positives.

BRIEF DESCRIPTION OF THE DRAWINGS

These and other features and advantages of the present invention will be more fully understood by reference to the following detailed description of illustrative embodiments of the invention in conjunction with the attached drawing in which like reference numerals refer to like elements and in which:

FIGS. 3B and 3C are alternative electrode configurations of the embodiment of FIG. 3A, each with two multi-function electrode sets (or "banks"), in practice of the invention.

SUMMARY OF THE INVENTION

Figure 1:
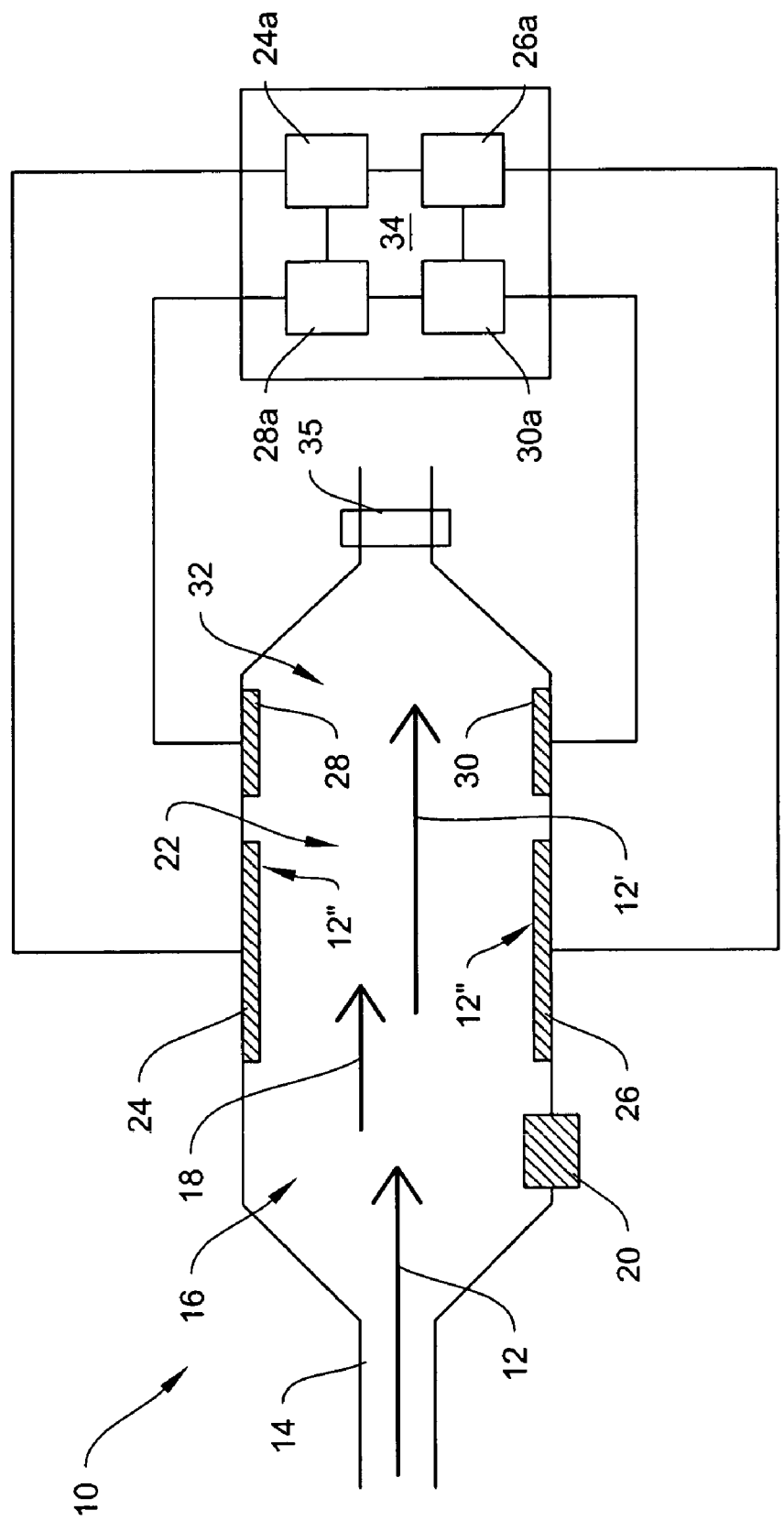
FIG. 1 is a schematic of a high field asymmetric ion mobility chemical analysis system.

The present invention is directed to an ion separator and detector that separates and detects ion species, configured in a compact package. Ion separation is based on ion mobility in a separation electric field. Embodiments of the present invention may operate with low and/or high RF or DC separation fields.

The present invention has application to FAIMS high field ion mobility spectrometry, which features selective neutralization of ion species. It also includes the recognition that improved identification or discrimination of compounds may be achieved by other use of ion neutralizations in the ion analysis process. In one embodiment, the present invention provides a high field ion mobility method and apparatus for separation and detection of ion species in a chemical sample. In another practice the present invention provides a trajectory-based field ion mobility method and apparatus. These modes may be used singly or together.

In an illustration of this embodiment, an ion separator-detector separates and detects an ion species based on ion trajectory when subjected to a transverse separator field. The field is created in an analytical gap separating two electrode banks within the separator-detector. The ions are transversely driven by the separator field in the gap. The ions are neutralized by contact with electrodes of the electrode banks. Any ions contacting the same electrode are of a common mobility species that is defined by their trajectory in the field. At least one of these electrodes serves as a detector electrode and species are detected based upon this contact. Thus separation and detection are both achieved in a single analytical space (the analytical gap between the separator banks of the separator-detector). The detection data can be processed and compared to a lookup table to identify the detected species.

It is significant that the ion separator performs trajectory-based separation of ion species by applying a transverse separation field in the separator, and that detection of these separated species occurs within that same separator-detector space based upon the trajectory of the ion species in the field. No additional detector arrangement is required, and a compact and efficient chemical analyzer is provided. One advantage of this arrangement is that separation and detection can be obtained all within a single simple electrode bank structure. Multiple processing environments and data comparisons are not required. One other advantage is that using multiple electrodes in the electrode banks enables simultaneous detection of multiple ion species. This provides for a fast device with high throughput.

In an alternative compact device of the invention, the detector is downstream of the analytical gap and detection continues based on trajectory aspects of the separated ion flow. The detector can be a series of segments in the downstream flow path. An advantage of this configuration is separation of the detector from influence of the filter field, which may be desired.

The present invention has application to FAIMS high field ion mobility spectrometry and includes the recognition that improved identification or discrimination of compounds may be achieved by more complete and innovative use of ion neutralizations in the ion analysis process. In one embodiment, the present invention provides a high field ion mobility method and apparatus for separation and detection of ion species in a chemical sample. In another practice, the present invention provides a field ion mobility method and apparatus for simultaneous separation and detection of multiple ion species in a complex chemical sample. Yet other embodiments are also provided. Embodiments of the invention include gas-driven or field-driven ion transport.

The present invention makes possible rapid identification of a wide range of compounds, including compounds that are difficult to identify by conventional means. This field ion mobility spectrometer can perform substantive quantitative analysis of complex mixtures in essentially real-time. (For purposes of this disclosure the concepts of "rapid" or "fast" may also be referred to as "real-time" or "near real-time"; while these are relative terms, detection within a fraction of a second or even within a second or a few seconds is certainly contemplated within these concepts and will be understood as being within the scope of the invention.)

In one embodiment, a bank or banks (i.e., a set or sets) of electrodes are formed along an ion flow path (i.e., flowing in a drift tube), and the electrodes interact to form an integrated ion separator-detector. At least a pair of opposed electrodes form separator electrodes between which the separation field is formed. At least one electrode is a detector electrode. In a multiple electrode embodiment, the separator-detector enables separation and detection, preferably simultaneously, of a plurality of distinct species of ions in a chemical mixture based on trajectory of the ions according to their mobility differences in the high field.

In an illustration of the invention, the separator electrodes face each other over the ion flow path, and at least one of the banks also has at least one detector electrode. The at least one detector electrode may be one of the separator electrodes or may be a separate electrode adjacent to a separator electrode. Preferably this all occurs in the ion separation region in the analytical gap formed between multiple separator electrodes. (The separator is a filter. The separator-detector may also be referred to as a filter-detector. The separator field may also be referred to as a filter field.)

In one preferred embodiment, multiple electrodes are provided on each bank. Each of these banks has a plurality of electrically isolated separator electrodes and these electrodes also function as detector electrodes. In another embodiment, detector electrodes are interspersed with the separator electrodes in a bank or banks of electrodes. In an embodiment of the invention, all of the electrodes of the banks can be independently accessed and controlled.

A preferred apparatus includes a source of charged ions, representing compounds in a sample to be analyzed, a housing defining an ion flow path (i.e., a drift tube) and a plurality of electrodes forming electrode banks along the flow path. Each bank includes at least one separator electrode, preferably multiple separator electrodes, with these electrodes facing each other over the flow path downstream from the ion source. The charged ions flow between the electrode banks in the flow path. One of the banks further includes at least one detector electrode, and preferably there are a plurality of detector electrodes, wherein the detector electrodes are for detection of ions according to their trajectories in the field.

A controller is provided for application of drive voltages to the separator electrodes for inducing the electric field in the analytical gap between the separator electrodes. The charged ions are subjected to the field, and the field imparts a respective trajectory to a respective charged ion according to ion mobility characteristics of the ions, which reflects the field effect and the ion flow rate in the filter field. Preferably the field is high (e.g., at or above 5000 v/cm$^2$). In one illustrative practice, a high field was formed in a 0.5 mil analytical gap separating the separator electrodes; the RF maximum voltage was operated at about 1500v-p-p.

In a preferred embodiment, a bank of electrodes includes a plurality of multi-use separator electrodes. These multi-use electrodes provide the separator field of the invention and also can be monitored for ion neutralizations; in this latter sense they perform the function of detector electrodes. This multi-function bank preferably is mounted facing a second bank across the flow path, with the separator field generated between these banks. In an alternative embodiment, separator and detector electrodes in the electrode bank are interspersed and as a team perform the multiple functions of separating and detecting. Thus the electrode banks are multi-functional.

In one embodiment, a set of electrodes performs both separator and detector functions simultaneously, and multiple species of ions are separated and detected simultaneously. In another embodiment, separator electrodes are interspersed with detector electrodes, and still multiple species of ions can be separated and detected simultaneously. In any case, in a preferred embodiment of the invention, each of the electrodes performing a detection function is coupled to a respective narrow bandwidth amplifier. Each of these amplifiers can be tune to a particular field condition, wherein each can be focused on detection of a particular ion species of interest.

The result of using such narrowband amplifiers is relatively low noise in the detection process and relatively high detection sensitivity, such as compared to prior art conventional FAIMS. In practice of the invention, conventional wider bandwidth amplifiers could be used where each detector needs to be able to scan a full spectrum. This would be a general purpose application of the invention.

However, since embodiments of the present invention enable each detector to be dedicated to a narrow range of interest (in view of its physical location along the flow path and its trajectory-based detection function) the ability to scan a complete spectrum of compounds (i.e., associated with a wide range of compensation voltages) in the sample is not needed. This would be a dedicated use application of the invention, and would enable a fast response system.

In embodiments of the present invention, the ions are propelled in the flow path by control of ion flow, such as control of a carrier gas transport, for example. Further embodiments of the invention include electrodes formed on spaced-apart substrates that define the enclosed internal flow path between the electrodes. The result is a light-weight and compact spectrometer with high sensitivity and capable of real-time analysis of a complex chemical sample.

In a preferred practice of the invention, the ionized sample may include both positive and negative ions which are carried to the separator. This is significant because an ion species may include both positive and negative ions. A preferred analysis may include evaluation of both modes. In a preferred embodiment of the invention, the separator-detector detects both positive and negative ions simultaneously, according to trajectory. This extra information provides improved and rapid species identification with low false positives.

The present invention may be practiced in several modes. It may be operated as a trajectory-based ion separator, with or as a FAIMS device, or with or as a hybrid trajectory-FAIMS-based separator-detector. Separations and detections may be made in any one or any combination of these modes.

In one practice of the present invention, a spectrometer is capable of identification of numerous compounds simultaneously without the need for the compensation or scanning of conventional FAIMS. This embodiment features at least one high field ion mobility separator-detector electrode bank, where the electrode bank is multi-functional and separating proceeds based on ion trajectory in the analytical gap between the electrode banks. For a flow of ions traveling at a given flow rate, the trajectory of a particular ion in that flow, as it is subjected to the high field transverse to the ion flow, is a function of ion size, cross-section, charge and mass. This function is generally referred to as high-field mobility.

Generally speaking, a particular ion species will have a unique field mobility, which can be determined as a "mobility signature". We have found in FAIMS systems that an expression of the high field-dependence of ion mobility, the so-called alpha coefficient, expressed as a function of field, can be used to generate a unique alpha function that is inherent for that species: its unique high-field mobility signature. This function expresses a characteristic signature for the ion species. This detection and identification strategy is set forth in detail in our copending application Ser. No. 10/187,464, filed Jun. 28, 2002, incorporated herein by reference. These signatures may be used as part of or to supplement species identification in practice of the invention. The signature can be determined for a detected unknown compound based on the high field conditions that are used, and then this can be used to make an identification according to a lookup table of stored known signature data associated, or by other known identification techniques.

In an illustrative FAIMS application of the alpha function, ion species are identified based on the mobility dependence of the species under various field conditions. For any given set of field conditions, the field strength and compensation can be correlated with an alpha value. Since field strength and compensation value are known at the time that a detection is made, and the alpha can be determined, then lookup of the species associated with that alpha enables precise species identification.

In practice of the present invention, an ion species is identified based on its field mobility signature. In one embodiment, a DC voltage is applied to a first separator electrode on one bank with an opposed electrode on the opposed bank being at ground, the electrodes being separated by an analytical gap of 0.5 mm. In another embodiment the DC is floating between the electrodes and is pulsed. In one embodiment, a high DC field is presented between these electrodes and mobility difference behavior of the ions in this field can be detected as set forth herein.

In another embodiment, an asymmetric RF voltage applied to the ion separator electrodes in the range of about 900 to about 1.5 kV (high field condition), followed by a low voltage of about −400 to −500 V (low field condition). The system analytical gap separating the electrodes was 0.5 mm. Other embodiments are also within the scope of the invention.

In any event, it will be appreciated that the ability to perform a variety of high field analytical events on a sample or samples enables the collection of substantial species-specific detection data. The result is more accurate identifications with fewer false positives.

Systems of the invention can be switched between various modes of operation. In one embodiment, in a trajectory mode, ions are separated based on differences in field mobility behavior and on trajectory as they deposit their charges on detector electrodes of the separator-detector array or on downstream detector electrodes, which may be a bank of detector electrodes. The field may be DC or RF, low or high. Preferably ions are neutralized as they hit an electrode; wherein an ion species will be neutralized on a particular detector electrode according to ion trajectory in the field, and according to the ion transport flow rate. The ion species can be identified thereby.

In one embodiment of a switchable system of the invention, we can operate in an ion-mobility based mode (FAIMS or even conventional IMS) mode or in an uncompensated field mode. Ions are separated based on differences in field mobility behavior and are detected upon depositing their charges on detector electrode(s). The separation is ion mobility based and may include the benefit of trajectory affects.

The detection data is processed and an indication of presence of the ion species can be made, such as by illuminating a red light in a dedicated system. In another system an identification of various compounds in the sample can be made even where the system is not dedicated to a specific ion species detection. In a preferred embodiment, species identification is by the high field mobility parameter (alpha).

There are several modes of operation of the invention for sample characterization. As an illustration, for a given sample to be analyzed, one mode of operation may be adjusted to provide a first set of detection data for a first set of conditions while a second mode of operation may be adjusted to provide a second set of detection data for the same or for a second set of conditions. For example, high field trajectory-based detection might be used to detect isomers of a compound while the FAIMS mode might be used to detect monomers of a compound in a sample, or vice versa, according to the character of the target (suspected) analytes of interest. Combination of resulting detection data enables rapid characterization of the components in a chemical sample with a high degree of confidence.

These and other innovations of the invention will be appreciated by a person skilled in the art by reference to the specification set forth below.

DETAILED DESCRIPTION OF A PREFERRED EMBODIMENT

A FAIMS spectrometer 10, shown in FIG. 1, receives a chemical sample 12 at inlet 14. The sample flows into ionization region 16 in flow path 18, where it is ionized by ionization source 20. Ionization of the compounds in the sample creates ionized molecules ("ions") that are carried by a transport or carrier medium into the ion filter 22 in flow path 18 between filter electrodes 24, 26. Embodiments of a compact and efficient high field asymmetric ion mobility spectrometer are disclosed in U.S. Pat. No. 6,495,823 (ion transport by carrier gas) and in U.S. Pat. No. 6,512,224 (electric field ion transport), incorporated herein by reference. Systems of the invention may include plate type or cylindrical type electrodes and the like.

A compensated, asymmetric high electric field is generated between the filter electrodes that has differential impact upon mobility of the ions according to their size, charge and cross-section, and mass. This mobility difference produces a characteristic net transverse displacement of the ions as they travel longitudinally through filter 22 between the filter electrodes 24, 26.

The transverse displacement results in ions driving into the filter electrodes and being neutralized. However, in the presence of a low voltage DC compensation bias applied to the field, a particular ion species 12' will be returned toward the center of the flow path and will pass through the filter to be detected on electrodes 28 or 30 of detector 32. While ion species 12' is returned toward the center of the flow path and passes through the filter to detector 32, all other species 12" will not be sufficiently compensated and will collide with the filter electrodes and will be neutralized. This elimination of ion species by neutralization is an essential part of conventional high field asymmetric ion mobility isolation of an ion species of interest. The latter is passed by the ion filter unneutralized for downstream detection.

Each detector is preferably supported by an amplifier 28a, 30a, wherein the signal generated by the ions depositing their charges on the detector electrodes will be amplified and delivered to the system controller for processing. The detection signal indicates the presence of a detected target ion species. Such detection event is correlated with the RF field conditions and DC compensation level and which is matched with a table of data associated with known species for identification of the detected species. Preferably the identification is based on the high field mobility of the detected species as expressed in its associated alpha function. Furthermore, the detection signal intensity relates to the quantity of detected ion species. Therefore this method is both qualitative and quantitative.

If multiple compounds are in the sample, then multiple tests may be run, in sequence, each with an appropriate compensation level, or else a scan can be run through different compensation levels. By sweeping the compensation over a predetermined voltage range, a spectrum can be analyzed, one step after another, to cover a range of mobilities to detect various compounds that may be in the sample.

The above FAIMS spectrometer is adequate for real-time analysis in many applications. However, for a given set of field conditions and compensation level, it is possible that ions representing multiple species may be passed to the detector. It is desirable to apply additional strategies for a compact spectrometer that can render real-time detection of multiple chemical compounds simultaneously with minimal false positives.

Therefore, one embodiment of the present invention is directed to an ion separator and detector that separates and detects ion species in a compact package. In one embodiment this package may also be operated as a FAIMS detector. This system may operate with low and/or high RF or DC fields.

In an illustration of this embodiment, an ion separator-detector separates and detects an ion species based on ion trajectory when subjected to a transverse separator field. The field is created in an analytical gap separating two electrode banks within the separator-detector. The ions are transversely driven by the separator field in the gap. The ions are neutralized by contact with electrodes of the electrode banks. Any ions contacting the same electrode are of a common mobility species that is defined by their trajectory in the field. At least one of these electrodes serves as a detector electrode and species are detected based upon this contact. Thus separation and detection are both achieved in a single analytical space (the analytical gap between the separator banks of the separator-detector). AS will be appreciated by a person skilled in the art, the detection data can be processed and compared to a lookup table to identify the detected species, with knowledge of the ionization function, applied field, flow rate, pressure, humidity, etc.

In a preferred compact package of the invention, the ion separator performs trajectory-based separation of ion species by applying a transverse separation field in the separator, and detection of these separated species occurs within that same separator-detector space based upon the trajectory of the ion species in the field. No addition detector arrangement is required, and thus a compact and efficient chemical analyzer is provided.

One advantage of this arrangement is that separation and detection can be obtained all within a single simple electrode bank structure. Multiple processing environments and data comparisons can be used but are not required. One other advantage is that using multiple electrodes in the electrode banks enables simultaneous detection of multiple ion species by trajectory. This provides for a fast device with high throughput.

Referring again to the device of FIG. 1, it will be appreciated that we can obtain detection data by monitoring ion deposits (neutralizations) at detectors 28, 30. Amplifiers 28a, 30a, couple the detector electrodes to the controller for collection of this detection data. Optionally, we also can monitor ion neutralizations at separator electrodes 24, 26, and optional amplifiers 24a, 26a (shown added in dotted outline) may also be provided for collection of the ion neutralization data at separator electrodes 24, 26. The result is more complete detection data for enhanced chemical identification.

One limitation with the ion neutralization data collected at separator electrodes 24, 26, is that there is relatively little specificity in such data collection, since many rejected ion species may be neutralized on the separator electrodes at any one time while a selected ion species of interest is being returned to the ion flow according to field compensation.

Figure 2:
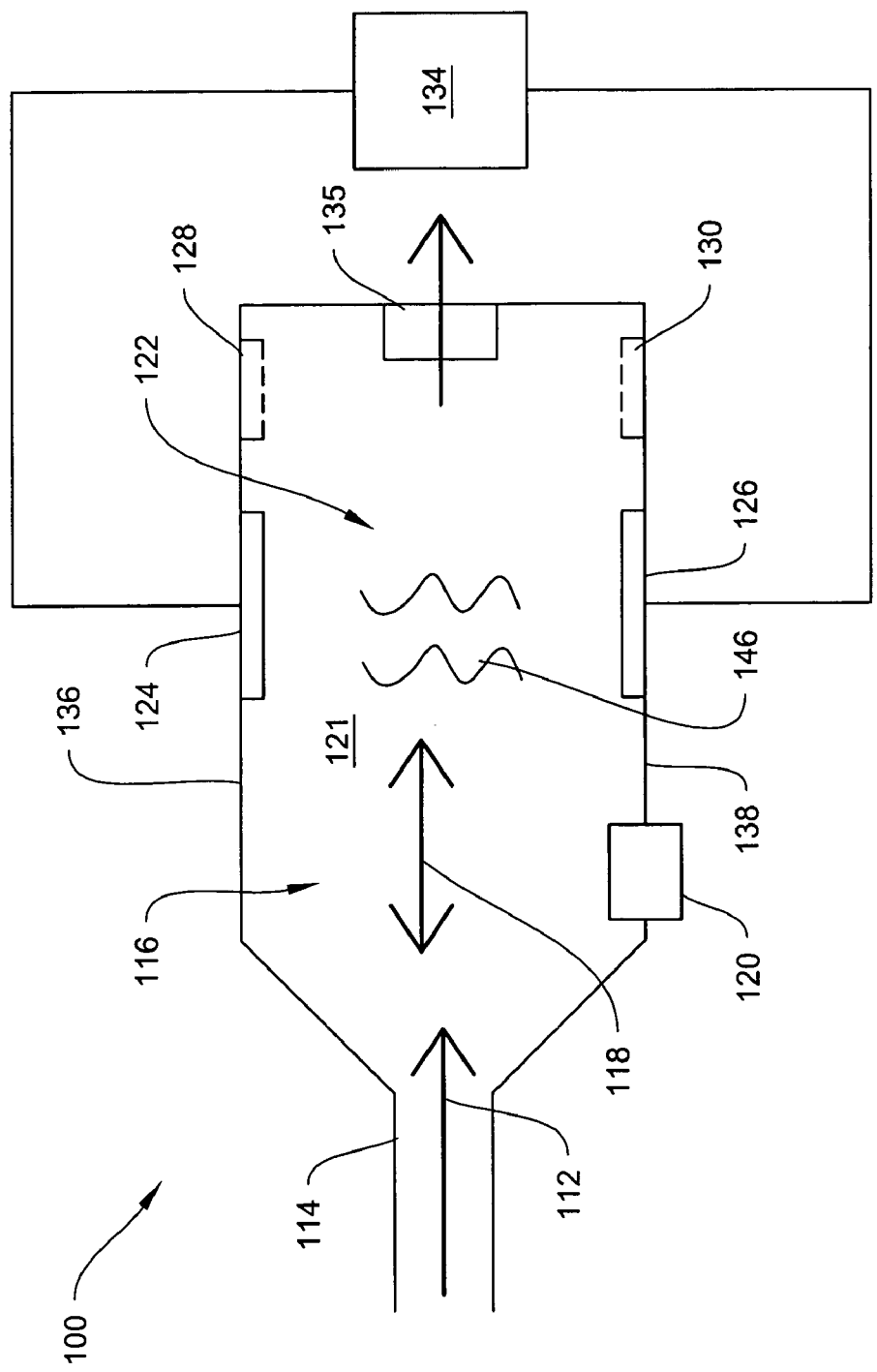
FIG. 2 is a schematic of an illustrative embodiment of the present invention.

Therefore, in practice of an embodiment of the invention, as shown in FIGS. 2–3, we provide a bank or banks of electrodes wherein each electrode can be driven as a separate electrode of a separator-detector, each for obtaining separate neutralization detections for a given ion species.

To that end, an illustrative embodiment of a high field ion mobility spectrometer 100 in practice of the present invention is shown in FIGS. 2–3. A gas sample 112 containing a variety of chemical compounds is introduced through inlet 114 into ionization region 116 at one end of flow path 118.

The compounds in the sample are ionized in the ionization region as the sample is carried by a carrier gas along the flow path. Ionization of the compounds creates ionized molecules ("ions"), and these in turn are carried by the carrier gas into a high field ion mobility separation region 121 (i.e., the analytical gap) between electrodes of a separator-detector assembly 122. Ionization at source 120 proceeds wherein ions flow in the flow path in a controlled manner, such as in the center of the flow path between the electrodes in the separation region, i.e., in the analytical gap G between the electrode, for further processing. In one illustration, a high electric field is generated between the separator electrodes in the separation region to assist in species detections. This is based on the observation that the field has differential impact upon behavior of the ions according to their size, charge and cross-section, and mass.

Figure 3A:
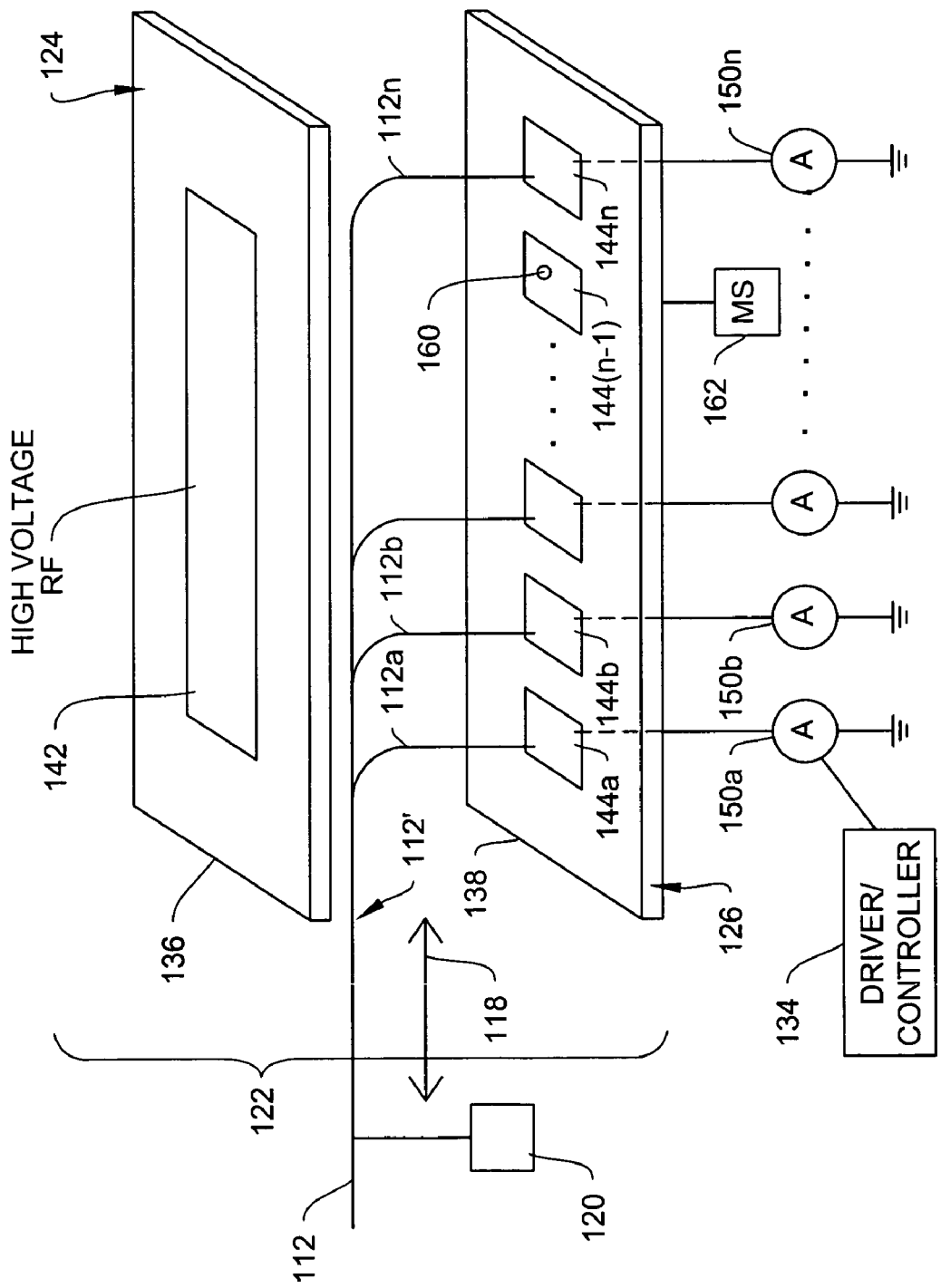
FIG. 3A is a schematic of the separator-detector of the embodiment of FIG. 2 in practice of the invention.

Thus separator-detector assembly 122 includes separator electrodes and detector electrodes within this separator region 121. Referring also to FIG. 3A, an illustrative separator-detector assembly 122 includes two electrode banks 124, 126 formed on insulated substrates 136, 138. In this illustrative embodiment, electrode bank 124 includes a single electrode 142. The single electrode 142 of bank 124 serves a separator function but it also serves a detection function. Electrode bank 126 includes a plurality of electrodes, 144a–144n. At least one of electrodes 144a–144n serves a separator function and any of these electrodes also serves a detector function.

The substrates include sidewalls, the result of which is to provide a spacing arrangement that both packages the flow path and sets the electrode gap, all in a low-parts count and volume manufacturable package.

Driver-controller 134 is provided for application of drive voltages to the electrode banks for inducing electric fields therebetween. Thus in a high field embodiment, driver-controller 134 applies a high voltage to electrodes 142 and 144a–n to generate a high field 146 between the electrode banks 124, 126 of the separator-detector 122, and transverse to the ion flow in flow path 118. The field can be RF, DC, strong or weak, any of which can be used to create a known mobility profile of ions to be detected.

It will be appreciated that in practice of embodiments of the invention, ions species can be identified by low and/or high field mobility signatures. In practice of an embodiment of the invention, the ionized compounds 112a–112n in ionized sample 112' flow between banks 124, 126 where they are subjected to the separation field 146, preferably a high field.

The high field may be, for example, a high asymmetric RF field or a high DC field, and enables generation of a high field mobility signature. The field may be low, whether as an RF field or as a low DC field, and enables generating a low field mobility signature. The field may be an asymmetric, high-low varying RF field, from which mobility differences can be obtained for species identification; when such field is compensated, then FAIMS-based differential mobility identifications can be made. These high, low and varying field identifications are based on detection data collected in practices of the invention. It will thus be appreciated that species identification may be made in practices of the invention using one such detection data collection or combinations of such data collections.

Figure 3B:
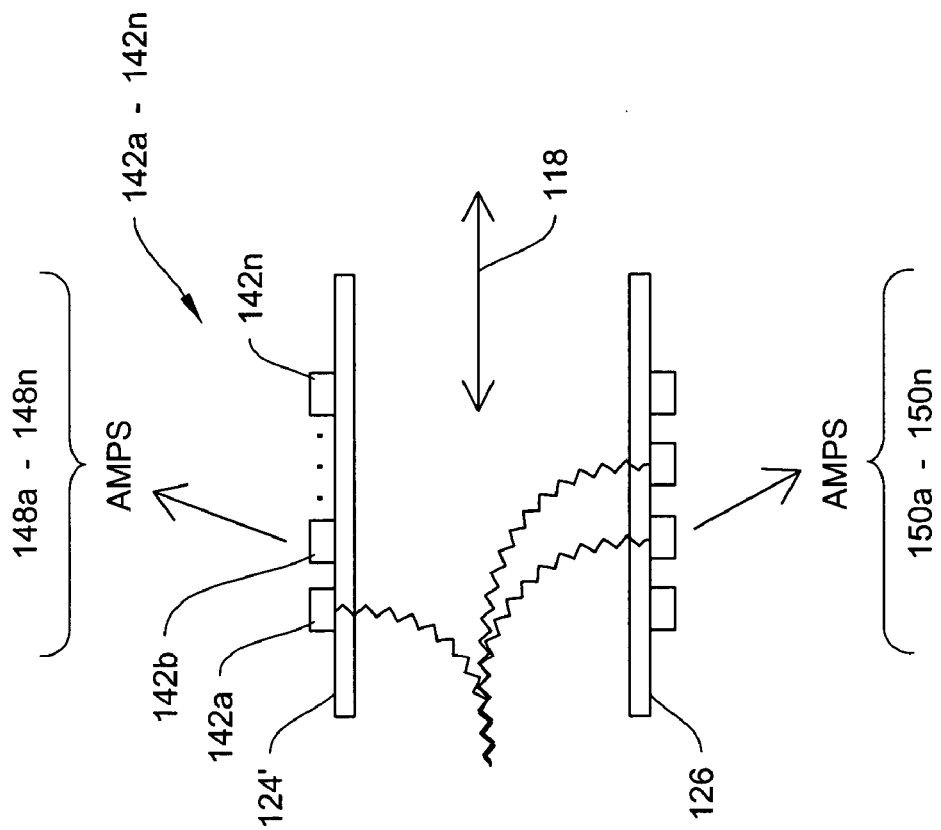

In a further embodiment of the invention, the single electrode of bank 124 in FIG. 3A is replaced with a structure like the multiple electrode structure of bank 126. More particularly, as shown in FIG. 3B, a multi-functional bank 124' includes several electrodes (e.g., 142a–142n) facing bank 126 over flow path 118.

In the invention, charges being deposited (neutralized) on selected electrodes are monitored to obtain species detection data. Thus a sample may have detection data from a plurality of electrodes simultaneously indicating various chemical constituents.

The electrodes may be biased, floating, tied to ground, or the like. The electrodes of bank 124' perform a like function described above for the electrodes of bank 126, with the intent that ions may be propelled to any of appropriately placed electrodes of either bank according to mobility, trajectory and/or polarity consistent with the principles set forth herein.

In such embodiment, the charged ions are subjected to the high field, and the field imparts a respective trajectory to a respective ion according to ion mobility characteristics of each ion. As a benefit of the spatial arrangement of the electrodes 142a–142n, 144a–144n in the separator-detector banks 142, 144, the ions are transversely deflected by the high field, and, according to flow rate and the high field mobility characteristics of each ion, the ions will separate out as species by their trajectory and will congregate and be neutralized on one of the electrodes based on the trajectory. This may be one of the electrodes of bank 124 or 126. Furthermore, for opposed detector electrodes, a pair may be oppositely biased, so that positive ions are detected by the negative biased electrode, and vice versa, the other electrode of the pair also acting as a deflector electrode. As a result, a polarity-based set of detection data may be obtained to augment species identification.

In an embodiment of the invention utilizing an asymmetric field, the high field 146 developed across separator electrodes 142, 144a–n alternate between high and low field strength conditions that causes the ions in the separator to move in response to the field, based on their high field mobility. This mobility difference in the field produces a net transverse displacement of the ions as they travel longitudinally through separator, and this imparts a characteristic trajectory to the ions for a given carrier gas flow rate.

In this illustration, the detection data is collected at the electrodes and via amplifiers 148a–148n, 150a–150n, and is delivered as species-specific detection data to the driver-controller 134 for analysis and species identification, such as by comparison to lookup tables.

In one embodiment, general purpose, wideband, amplifiers of FIG. 1 may again be employed in the embodiment of FIGS. 2–3. However because each of separate amplifiers may be dedicated to separate ones of the electrodes, and each looking at a narrower spectrum without the need for performing a wide scan, it is possible to use narrow-band amplifiers 148–150. Such narrow bandwidth amplifiers will be known to a person skilled in the art. The benefit is reduced noise in the detection process—thus resulting in higher detection sensitivity and/or improved species resolution. It will therefore be appreciated that each separator-detector electrode may be set to a narrow range of interest and need not be scanned as in conventional FAIMS.

Returning to FIG. 3, the mobilized ions 112a–112n are separated according to differences in ion mobility and according to their trajectory and as carried by the carrier medium at a given flow rate. In practice of the present invention, continuous data collection may be achieved for multiple species detections, simultaneously.

The detector circuits preferably include amplifiers 148a–148n, 150a–150n under control of driver-controller 134, to detect the deposited charges. These detections are correlated with field values and flow rates and ion species are identified based on field dependency characteristics, such as computed alpha values.

It will be understood that any of the electrodes of banks 124, 126 may be used as separator and/or detector electrodes, although the first two in sequence are likely to be separator electrodes. All of the electrodes on these banks may be individually biased, driven and monitored.

It will be further understood that the electrodes of the electrode banks can be used in various patterns, such as required for a dedicated detection application. As will be appreciated by a person skilled in the art, with software and computer integration, configurations can be adjusted even on-the-fly as needed.

It is noted that entry into the flow path from the inlet or from an aperture along the flow path, of either or both the carrier gas and/or the ionized sample, are within the scope of the invention. Furthermore, the present invention contemplates ion transport in the flow path as a fluid, whether gas-driven or field-driven.

Where FAIMS operation is used, compensation may be provided in a variety of manners, and as long as the ion flow is controllable. For example, flow rate change may be used as a substitute for compensation change for discriminating between species and for obtaining field mobility characteristics thereof. It is noted however, that in a preferred the trajectory-based system of the invention, using the spatial arrangement of the electrodes in the separator-detector electrode banks, there is no need for field compensation as is required in FAIMS devices.

As earlier discussed, the alpha function can state a characteristic ion mobility for a given ion species detection. The amount of charge detected relates to the intensity or quantity of that species. The actual detection event, regardless of intensity, can enable an alpha determination to identify the detected species for a given set of field conditions, such as generated in a compensated high-low varying RF filter field of a FAIMS device. Therefore in one optional practice of the invention, we calculate alpha according to field and then once the alpha is determined, a controller 134 compares this result to an alpha data store to identify the detected species. Alpha functions are only one example of species characteristics, detection and identification. In a further embodiment, we link field conditions, trajectory, flow rate, location of the detector electrode, as adequate data for defining a detected species.

If multiple detections are made along with a change in flow rate or other field conditions, then the actual alpha function can be determined for that detected species for identification of the detected species. In one modified FAIMS practice of the invention, in a given high field, at a first flow rate, a species is detected at a first electrode, say electrode 144b; now in the same field at a second flow rate, a second detection is made at a second electrode, say at electrode $144_{n-2}$. Thus ion mobility sensitivity to field changes or flow changes results in changes in ion trajectory. Since detections are made at a first and then at a second detector, we can use this behavior and detection data, correlated with the field and flow conditions, as a signature behavior for species identification. In short, rather than use changes in compensation voltage to detect species behavior, we use changes in flow rate in this example. We also can scan the flow rate to perform a full separation-detection scan.

In a carrier-gas driven embodiment of the invention, driver-controller 134 regulates the ion transport (e.g., carrier gas flow rate), such as by control of a pump 135 or the like. Pump 135 draws the sample and carrier gas through the separator and then provides a device exhaust. While the flow path is shown along a longitudinal axis, gas entry and exhaust may be at an angle to such axis, within practice of the invention. In the field-driven embodiment, the ion transport (i.e., flow) is controlled with an electric field that drives the ions (e.g., push or pull) through the separator.

In practice of trajectory-based embodiments present invention, ion neutralizations occur as part of a detection event. Data loss is thus avoided. As stated above, the net transverse displacement of the ions in the separator imparts a characteristic trajectory to the ions according to their mobility and flow rate. As a result, under controlled flow conditions, members of the same ion species will land on the same electrode, based on their characteristic trajectory. This is a characteristic mobility signature that enables species identification. The field may be compensated or not as long as a repeatable field dependency can be used for species identification.

In an alterative practice of the invention shown in FIG. 3C, in addition to or instead of the multi-use separator electrodes described above, detector electrodes 143a–n and 145a–n are formed adjacent to and interspersed with the separator electrodes (designated as F1–Fn, FF1–FFn) in electrode banks 124", 126". All of the electrodes on these banks may be individually biased, driven and monitored. This enables various pairs of electrodes (on the same bank or on opposed banks) to be driven according to the characteristics of any particular single or multiple target ion species of interest. The result is that the entire bank (or banks) of electrodes can be set to separate and detect chemical species, according to specific mobility and trajectory characteristics of various species, simultaneously, for a selected sample introduction and flow rate.

The electrode or electrodes on one bank or both may be held at ground or at any other potential that assists development of an adequate (RF or DC) field. The electrodes are controlled, monitored and/or driven by driver-controller 134. Furthermore, the electrodes on the multi-function bank may each be held at a different potential relative to each other, according to the ion species sought to be detected at each electrode.

It will also be appreciated that in an embodiment of the invention, as shown in FIGS. 3A and 3B, each multi-use separator electrode of the array of electrodes on bank 126 can be and preferably is simultaneously monitored by driver-controller 134 as a detector electrode. Thus, for example, the charges deposited on a separator-detector electrode (e.g., 144a) indicative of the presence of a known ion species (e.g., 112a) having a specific characteristic trajectory according to its specific ion mobility in the field at a given flow rate, will be detected. Indication (e.g., at a computer screen) of the detected and identified compound may be made. At the same time, the charges deposited on neighboring electrodes (e.g., 144b) can be monitored as indicative of presence of another ion species (e.g., 112b), and detection, identification and appropriate indication thereof can be made simultaneously.

If the filed condition is then changed, a second set of data can be detected at a second set of expected detectors and can be associated with the first set of data. The alpha function can be generated to better identify each detected species.

It will be appreciated that in practice of a trajectory based embodiment of the present invention, ions are neutralized as they deposit their charges on the separator electrodes. These deposits are then detected. In conventional FAIMS this same neutralization of unwanted ions would have been ignored and can result in data loss. Thus the present invention makes efficient use of available data. Furthermore, simultaneous detection of species and use of narrow bandwidth amplifiers results in a spectrometer with high sensitivity and high selectivity.

In the trajectory-based practice of the invention, robust test results can be achieved in a single evaluation cycle. A sample thus can be analyzed rapidly, in a few seconds or even in less than a second, which is critically important where time or sample quantity are limited. This is achieved without the narrowing of the detection candidates by neutralization as has been considered essential to successful operation according to conventional compensated high field asymmetric ion mobility practices.

In one practice of the invention a separator-detector does not need downstream detectors. In a further practice of the invention, optional detector electrodes 128, 130 are provided as shown in dotted outline FIG. 2.

This apparatus can be used as a FAIMS spectrometer in a second mode of operation, by applying a compensated high field asymmetric signal to the separator electrodes with detections made at detectors 128, 130, such as disclosed in U.S. application Ser. No. 10/321,822, incorporated herein by reference.

Therefore an apparatus of the invention can be used in multiple modes. These may includes varieties of RF and DC field operation. In one embodiment, Mode 1 is the above described separator-detector mode of operation and Mode 2 is a FAIMS mode of operation. Because each mode will provide different detection data, their combination will avail a powerful detection and identification system. Now substantial data can be obtained for rapid and reliable species identification. It will be further appreciated that these modes can also include alternative or additional operations, such as one at low and one at high field values, as will be appropriate for species of interest.

It will be further appreciated that electrodes 128, 130 may be provided as members of the set of electrodes on banks 124, 126, such as electrodes 142n, 144n. In such embodiment, driver-controller 134 may be utilized to program the function of each electrode according to user needs for the assigned mode of operation.

In a further embodiment of the invention, electrodes 142a, 144a of electrode banks 124, 126 are separated from the rest of the banks of electrodes and the high field is developed between these separated electrodes 142a, 144a. Additional electrodes are provided in the banks downstream from the separator electrodes and form a series of detector electrodes. These detector electrodes are selected from electrodes 142b–142n, 144b–144n, and are for detection of ion species according to their high field ion mobility and the transport flow rate. These detector electrodes are spatially separated along the flow path so that common ions of a given species having common trajectories will contact and deposit their charges on common detector electrodes, according to the species-specific high field ion mobility and the carrier flow rate.

In one embodiment, a high DC voltage is applied to the separator electrodes to achieve the high field and ion neutralizations are monitored on the detector electrodes via associated amplifiers. Ion neutralizations also may be monitored on the separator electrodes for collection of additional analytical data, but this is not required. Again, driver-controller 134 determines the mode of operation for a given analysis.

These detections are preferably analyzed based on alpha characteristics discussed above. However, in an alternative embodiment, the mere separation by trajectory and landing on a particular detector all by itself may be adequate detection information, for a given high field and flow rate, so as to be able to issue an indication of the presence of an identified chemical in a sample. This present invention is versatile and flexible and variations of the above will be understood by a person skilled in the art to also be within the spirit and scope of the present invention.

It will be further appreciated that in a preferred embodiment, driver-controller 134 includes drivers, amplifiers, power supplies, microprocessors, displays, interfaces, and the like, and enables real-time user configuration of the system. Driver-controller 134 may have a combination of functions. Among these functions is generating and applying the high field, controlling flow rate and monitoring electrodes. Driver-controller 134 controls detection of the charges that the ions have deposited, which function may also include biasing of the detector electrodes and using opposite electrodes as deflector electrodes (e.g., positive bias deflector deflects positive ions toward negatively biased detector electrode) and also controls evaluation of the detection signal for identification of the detected ionized compounds. The latter may include comparison of the detection data with known detection data stored in a lookup table. Species identification may be made upon a match of these data, using the alpha parameter and alpha function of electric field or by other algorithms.

It will be further appreciated that the electrodes shown herein are planar and parallel, by way of illustration and not by way of limitation. It will be appreciated that other configurations of electrodes are also within the scope of the invention, including non-planar and non-parallel electrodes. For example, cylindrical or curved electrodes may be used in one practice of the invention. Furthermore, while the disclosed banks can provide a supply of electrodes that enable multiple configurations, still other configurations may be anticipated. For example, the electrodes can be made with each succeeding electrode being closer or further apart from its upstream neighbor to accommodate a desired trajectory pattern. Still other configurations are also within the scope of the invention.

It will now be appreciated that the present invention discloses method and apparatus for field ion mobility spectrometry. A preferred system includes an input section, a combined ion separator-detector section, and a control section. Separation proceeds under influence of compensated or uncompensated field with a given ion flow, with detection integrated into or adjacent to separator electrodes in the flow path, for producing accurate, real-time data for identification of a broad range of chemical compounds simultaneously.

The present invention may be produced in a compact package. This package can be manufactured using high volume techniques, resulting in favorable per unit costs and yet producing results comparable to expensive analytical equipment. These devices may be manufactured using known electronic package manufacture techniques. Spectrometers according to the invention provide the ability to apply highly effective analytical equipment both in the field and in the laboratory environment at reasonable cost.

The present invention is capable of detecting a broad range of chemicals. We can detect, discriminate and identify compounds and constituents thereof, including VOCs, ketones, NOX, SF6, halocarbons, biological materials, and the like, in various mixtures and concentrations. In a particular embodiment we also have benefited from doping compounds using various dopants, such as acetone and even moisture content.

In a further embodiment of the invention, a mass spectrometer is optionally provided for making additional species identifications. As shown in FIG. 3A, at least one detector electrode, such as electrode $144_{n-1}$, is optionally a guiding electrode that enables an ion species to be passed to the mass spectrometer (MS) for detection. For this purpose, electrode $144_{n-1}$ is provided with an aperture 160 which is aligned with the inlet 162 to the mass spectrometer. An ion species separated according practice of the invention and having a trajectory which directs it toward colliding with electrode $144_{n-1}$ can be passed through the electrode at aperture 160 into the MS inlet 162. At the same time, detections may be made on electrode $144_{n-1}$, wherein the combination of detections results in more accurate species identifications.

Various modifications of the specific embodiments set forth above are also within the spirit and scope of the present invention. It will be further appreciated that the present invention is operable with gas and liquid samples, even though for convenience the illustrative examples above refer to gas samples carried in the carrier gas flow. Therefore, the examples and embodiments disclosed herein are shown by way of illustration and not by way of limitation. The scope of these and other embodiments is limited only as set forth in the following claims.

What is claimed is:

1. A field ion mobility analytical system comprising:
a pair of electrode banks defining between them a flow path,
an ion separator and an ion detector, said separator and said detector for making trajectory-based ion species identification of ions flowing in said flow path between said banks, said electrodes being separated by an analytical gap,
each said bank comprising at least one separator electrode for forming said ion separator, at least one said bank having a plurality of electrodes, at least one of said plurality of electrodes comprising a detector electrode,
an electrical controller input for applying a time-varying voltage to said ion separator and generating a transverse time-varying electric field between said separator electrodes while the ions are flowing along the flow path for controlling the paths of said ions in said separator, said field causing selected ions of said flow of ions to contact said detector electrode based on ion mobility in the field and consequent ion trajectory,
said ions contacting said detector being identifiable based at least in part on said trajectory.

2. System of claim 1 further comprising an analytical package, said package forming said ion separator, said ion detector and said banks associated with said flow path.

3. System of claim 2 wherein said banks are spaced apart forming an analytical gap.

4. System of claim 3 wherein said gap is about 0.5 mm between facing electrodes on said banks.

5. System of claim 1 wherein said plurality of electrodes comprises a plurality of detector electrodes.

6. System of claim 1 further comprising at least one low noise amplifier, wherein said detection at said detector electrode is communicated to said controller via said amplifier.

7. System of claim 1 wherein said electrodes form an integrated ion filter-detector for simultaneous detection of distinct species of ions based on their trajectory according to their mobility in said asymmetric field, and wherein said field includes a RF field.

8. System of claim 1 further comprising a detector downstream from said banks for detecting ions that exit said separator.

9. System of claim 1 wherein said detector includes a plurality of segments, said segments separated along said flow path to spatially detect said ions according to their trajectories.

10. A high field ion mobility spectrometer for analysis of compounds in a sample, comprising:
a source of charged ions representative of compounds in a sample,
an ion flow path, a plurality of electrodes forming banks along said flow path, said banks facing each other over said flow path down stream from said source, said charged ions flowing between said banks in said flow path, each said bank including at least one filter electrode, a controller input for application of time-varying voltages to said filter electrodes for inducing a time-varying electric field between said filter electrodes while the ions are flowing along the flow path, said charged ions being subjected to said field between said banks, said field imparting a respective trajectory to a respective charged ion according to ion mobility characteristics of said respective charged ion, and at least one of said banks defining at least one detector electrode, said detector electrode for receipt of charge deposits from species of said charged ions having common trajectories.

11. The spectrometer of claim 10 wherein said at least one of said banks having said at least one detector electrode comprises a multi-function bank of electrodes and faces the other said bank across said flow path.

12. The spectrometer of claim 11 wherein said multi-function bank comprises an array of filter electrodes, wherein one of said filter electrodes is also said detector electrode.

13. The spectrometer of claim 11 wherein said multi-function bank comprises an array of filter electrodes, wherein said filter electrodes are detector electrodes.

14. The spectrometer of claim 11 wherein said multi-function bank comprises an array of detector electrodes, wherein said array of detector electrodes is formed interspersed with said filter electrodes.

15. The spectrometer of claim 10 wherein said mobility characteristics are based on ion features including size, charge, and cross-section of said charged ions.

16. The spectrometer of claim 10 wherein said ions are carried in a carrier gas in said flow path.

17. The spectrometer of claim 10 wherein said ions are electrically propelled in said flow path.

18. The spectrometer of claim 11 wherein said multi-function bank comprises an array of detector electrodes, wherein said array includes said at least one detector electrode, said controller enabling simultaneous detection of ion species on a respective one of said detector electrodes based on differences in trajectory.

19. The spectrometer of claim 10 wherein said electrodes form an integrated ion filter-detector for simultaneous detection of distinct species of ions based on their trajectory according to their mobility in said time-varying field.

20. Method for identification of a chemical in a sample, comprising the steps of:
i) ionizing the sample,
ii) flowing the sample as a flow of ions along a flow path between a series of electrodes,
iii) providing a time-varying electric field between said electrodes while the ions are flowing along the flow path and generating mobility behavior of said ions,
iv) separating said ions according to species, said separation based on said behavior in said field as expressing mobility characteristics of said species, and
v) providing an ion separator and an ion detector, said separator and said detector including a plurality of electrodes in said series of electrodes, for making trajectory-based ion species identification.

21. Method of claim 20 further comprising the step of applying at least one high voltage to said ion separator and generating a transverse high electric field between said separator electrodes for controlling the paths of said ions in said separator, said field causing selected ions of said flow of ions to contact said detector electrode based on ion mobility in the high field and consequent ion trajectory, and said selected ions forming an ion species defined as having the same ion mobility and said selected ions contacting said detector electrode at said flow rate.

22. Method of claim 20 comprising identifying ion species based on a carrier flow rate and field conditions.

* * * * *